United States Patent
Hickey et al.

(10) Patent No.: US 9,187,526 B2
(45) Date of Patent: *Nov. 17, 2015

(54) PEPTIDE BASED INHIBITION OF CAPCNA INTERACTION IN CANCER

(71) Applicants: Robert J. Hickey, Lakeview Terrace, CA (US); Linda H. Malkas, Lakeview Terrace, CA (US)

(72) Inventors: Robert J. Hickey, Lakeview Terrace, CA (US); Linda H. Malkas, Lakeview Terrace, CA (US)

(73) Assignees: Robert J. Hickey, Lakeview Terrace, CA (US); Linda H. Malkas, Lakeview Terrace, CA (US)

( * ) Notice: Subject to any disclaimer, the term of this patent is extended or adjusted under 35 U.S.C. 154(b) by 93 days.

This patent is subject to a terminal disclaimer.

(21) Appl. No.: 14/182,550

(22) Filed: Feb. 18, 2014

(65) Prior Publication Data

US 2014/0296156 A1    Oct. 2, 2014

Related U.S. Application Data

(63) Continuation of application No. 12/279,028, filed as application No. PCT/US2007/062335 on Feb. 16, 2007, now Pat. No. 8,653,039.

(60) Provisional application No. 60/743,316, filed on Feb. 17, 2006.

(51) Int. Cl.
*A61K 38/03* (2006.01)
*C07K 4/00* (2006.01)
*C07K 7/06* (2006.01)
*C07K 14/47* (2006.01)

(52) U.S. Cl.
CPC .............. *C07K 7/06* (2013.01); *C07K 14/4738* (2013.01)

(58) Field of Classification Search
None
See application file for complete search history.

(56) References Cited

U.S. PATENT DOCUMENTS

| 5,935,797 | A | 8/1999 | Clayberger et al. |
| 6,420,335 | B1 | 7/2002 | Weichselbaum et al. |
| 6,613,878 | B1 | 9/2003 | Cox et al. |
| 8,653,039 | B2 * | 2/2014 | Hickey et al. ............... 514/21.7 |
| 2003/0162233 | A1 | 8/2003 | Malkas et al. |

FOREIGN PATENT DOCUMENTS

| WO | 96/35715 | 11/1996 |
| WO | 2006/116631 | 11/2006 |
| WO | 2007/002574 | 1/2007 |

OTHER PUBLICATIONS

Bennett et al. "Proliferating Cell Nuclear Antigen," Database: Uniport accession No. Q9GK19 (2001).
Roos et al. "Determination of the Epitope of an Inhibitory Antibody to Proliferating Cell Nuclear Antigen," Experimental Cell Research, 226(1): 208-213 (1996).
Huff et al. "Insights Into Native Epitopes of Proliferating Cell Nuclear Antigen Using Recombinant DNA Protein Products," Journal of Experimental Medicine, 172: 419-429 (1990).
Zhang et al. "The Interdomain Connector Loop of Human PCNA is Involved in a Direct Interaction with Human Polymerases 8," Journal of Biological Chemistry, 273(2): 713-719 (1998).
Search report issued in corresponding application No. PCT/US2007/062335 (2007).

* cited by examiner

*Primary Examiner* — Satyanarayana R Gudibande
(74) *Attorney, Agent, or Firm* — Whiteford, Taylor & Preston; Peter J. Davis

(57) ABSTRACT

Peptides derived from cancer specific isoform of proliferating cell nuclear antigen (caPCNA, also known as csPCNA) or from nmPCNA-interacting proteins interfere with intracellular protein-protein interaction, thereby causing a reduction in the proliferative potential of cancer. These peptides serve as therapeutic compositions to reduce the proliferation of cancer cells and also augment existing chemotherapeutic methods.

2 Claims, 4 Drawing Sheets

PEPTIDE BASED INHIBITION OF CAPCNA INTERACTION IN CANCER

CROSS-REFERENCE TO RELATED APPLICATIONS

This application is a continuation of U.S. patent application Ser. No. 12/279,028 filed Aug. 11, 2009, now U.S. Pat. No. 8,653,039 issued on Feb. 18, 2014, which is a continuation of U.S. nationalization under 35 U.S.C. §371 of international patent application no. PCT/US2007/062335, filed Feb. 16, 2007, which claims priority to U.S. Ser. No. 60/743,313, filed Feb. 17, 2006, the contents of which applications are herein incorporated by reference in their entireties.

TECHNICAL FIELD

This disclosure relates to peptide-based therapeutic compositions and methods to selectively target cellular components and processes involved in cancer proliferation.

BACKGROUND

Proliferating cell nuclear antigen (PCNA) plays an important role in the process of DNA replication, repair, chromosomal recombination, cell cycle check-point control and other cellular proliferative activities. In conjunction with an adaptor protein, replication factor C (RFC), PCNA forms a moving clamp that is the docking point for DNA polymerases delta and epsilon. Different isoforms of proliferating cell nuclear antigen (PCNA) that display both acidic and basic isoelectric points (pI) have been demonstrated. Analysis of PCNA by two-dimensional polyacrylamide gel electrophoresis (2D PAGE) from both malignant and non-malignant breast cells (referred to as non-malignant PCNA or nmPCNA) and tissues revealed the presence of an acidic form of PCNA only in malignant cells (referred to as the cancer-specific PCNA or csPCNA or caPCNA). This difference in isoelectric point between these two forms of PCNA, appears to result from an alteration in the ability of the malignant cells, to post-translationally modify the PCNA polypeptide and is not due to a genetic change within the PCNA gene.

Structural work examining the structure of the PCNA polypeptide to define the structural differences between the caPCNA and non-malignant cell isoform of PCNA revealed a region of the caPCNA protein that is uniquely exposed only in the cancer cell. An antibody was developed to a region of the cancer specific isoform of PCNA that is highly selective for the PCNA isoform expressed exclusively in cancer cells.

Proliferating cell nuclear antigen (PCNA) is a 29 kDa nuclear protein and its expression in cells during the S and G2 phases of the cell cycle, makes the protein a good cell proliferation marker. It has also been shown to partner in many of the molecular pathways responsible for the life and death of the cell. Its periodic appearance in S phase nuclei suggested an involvement in DNA replication. PCNA was later identified as a DNA polymerase accessory factor in mammalian cells and an essential factor for SV40 DNA replication in vitro. In addition to functioning as a DNA sliding clamp protein and a DNA polymerase accessory factor in mammalian cells, PCNA interacts with a number of other proteins involved in transcription, cell cycle checkpoints, chromatin remodeling, recombination, apoptosis, and other forms of DNA repair. Besides being diverse in action, PCNA's many binding partners are linked by their contributions to the precise inheritance of cellular functions by each new generation of cells. PCNA may act as a master molecule that coordinates chromosome processing.

PCNA is also known to interact with other factors like FEN-1, DNA ligase, and DNA methyl transferase. Additionally, PCNA was also shown to be an essential player in multiple DNA repair pathways. Interactions with proteins like the mismatch recognition protein, Msh2, and the nucleotide excision repair endonuclease, XPG, have implicated PCNA in processes distinct from DNA synthesis. Interactions with multiple partners generally rely on mechanisms that enable PCNA to selectively interact in an ordered and energetically favorable way.

The use of short synthetic peptides for the generation of polyclonal and monoclonal antibodies has been used with considerable success. Peptides are known to serve as chemo-attractants, potent neurological and respiratory toxins, and hormones. The peptides have also been used as affinity targets and probes for biochemical studies, and have provided a basis for understanding the characteristics and specific nature of discrete protein-protein interactions. In addition, peptide hormones exert potent physiological effects, and in some cases the active hormone is either a peptide that is contained within a larger protein or is processed and released from a precursor protein prior to exerting its physiological effect.

Peptides have been used to disrupt protein-protein interactions, by acting as highly specific competitors of these interactions. Biochemical studies employing peptide reagents advanced the use of peptides as therapeutic drugs capable of disrupting cell functions that require protein-protein interactions. Thus, specific cellular processes such as apoptosis and cell cycle progression, which are dependent upon discrete protein-protein interactions, can be inhibited if these protein-protein interactions are selectively disrupted. The replication of genomic DNA being dependent on protein-protein interactions is also susceptible to peptide-induced inhibition of these protein interactions.

In vivo DNA synthesis is a highly regulated process that depends on a myriad of biochemical reactions mediated by a complex series of protein-protein interactions. Cell division is dependent on the DNA synthetic process, and cancer cell growth is substantially sensitive to any agent that disrupts the regulation and/or the activity of the DNA synthetic machinery responsible for copying the cancer cell's genomic DNA. In addition, it was demonstrated that one signature of breast cancer is the induction of genomic instability, as transformed cells develop a highly aggressive metastatic phenotype. Genomic instability arises through a series of changes in the cellular DNA synthetic machinery that alters the fidelity with which DNA is synthesized.

Studies utilizing the carboxyl terminal 26 amino acids from the p21cip protein, (which is known to interact with the PCNA protein), demonstrated the ability of this peptide to disrupt the cellular proliferative process. This peptide fragment of p21 potentially disrupts one or more cellular processes utilizing PCNA and presumably interferes with critical protein-protein interactions that participate in the DNA synthetic process as well as the regulation of other cell cycle check-point controls and the induction of apoptosis.

Studies utilizing this peptide fragment of p21 have demonstrated the ability of the p21 peptide to activate a non-caspase associated apoptotic pathway. Similarly, studies involving a 39 amino acid peptide fragment of the p21 protein partially inhibited DNA replication in vivo, and suggest that this peptide fragment of p21 can stabilize the PCNA-p21 protein interaction leading to the decrease in DNA synthetic activity within the cell.

A synthetic peptide corresponding to residues 65-79 of the HLA class II sequence can inhibit cell cycle progression in a manner that is similar to that induced by rapamycin. This study indicates that peptides other than those derived from cell cycle regulatory proteins have the ability to modulate progression through the cell cycle.

In addition, computational chemical methods are being used to model specific regions of the PCNA molecule that may interact with other cellular proteins involved in cell cycle check point control and DNA synthesis. Regions of the cyclin-CDK complex may serve as templates to identify target sites for disrupting key cell cycle check-point control points that are essential for cell proliferation.

Use of synthetic peptides to inhibit cell proliferation and the process of selectively targeting cancer specific PCNA protein to mediate the inhibition of cell proliferation is needed to treat cancer. Peptidomimetic drugs that interact with an antigenic site or target site on caPCNA to disrupt specific protein-caPCNA interactions that are unique to the cancer cell are desired. Peptides derived from caPCNA specific epitopes, disclosed herein, significantly augment the cytotoxic effects of specific traditional chemotherapeutic regimens and consequently kill cancer cells in a highly selective manner.

SUMMARY

Peptides derived from specific regions or domains of non-malignant PCNA (nmPCNA) protein or cancer specific (caPCNA or csPCNA)-interacting proteins interfere with the interaction of cellular proteins with the PCNA protein in vivo. Specific amino acid sequences representing peptide fragments of the caPCNA protein disrupt the regulatory activity of PCNA and subsequently inhibit cancer cell growth through the disruption of functioning of cellular processes that require PCNA, including DNA replication, repair, chromosomal recombination, and cell cycle check-point control.

A method of selectively inhibiting in vivo interaction of a cancer specific isoform of proliferating cell nuclear antigen (caPCNA) with an intracellular protein in a malignant cell, the method includes the steps of:
  (a) providing an agent that selectively disrupts the interaction of the caPCNA with the intracellular protein;
  (b) administering the agent such that the agent contacts a population of cancer cells in vivo; and
  (c) inhibiting the interaction of caPCNA with the intracellular protein.

The agent can be either a peptide, peptidomimetic, small molecule or a combination thereof. In an embodiment, the agent is a peptide that includes an amino acid sequence LGIPEQEY (SEQ ID NO: 1). In another embodiment, the agent is a peptidomimetic that interacts with the caPCNA molecule at a target site comprising an amino acid sequence LGIPEQEY (SEQ ID NO: 1).

In an embodiment, the agent is a peptide that further includes a tag sequence. The tag sequence may include amino acid sequence RYIRS (SEQ ID NO: 38). Any translocation sequence is suitable for use herein.

In an embodiment, the agent is administered intravenously. In an embodiment, the agent is formulated in a therapeutic delivery system selected from a group that includes liposome, microparticle, and nanoparticle.

In an embodiment, the agent disrupts the interaction of caPCNA with an intracellular protein that is involved in a cellular process selected from a group that includes DNA synthesis, DNA repair, recombination, transcription, cell cycle checkpoint control, and apoptosis.

In an embodiment, the agent is a peptide molecule whose amino acid sequence is derived from an antigenic site on caPCNA. In another embodiment, the agent is a peptidomimetic molecule whose molecular structure corresponds to an antigenic site on caPCNA. In another embodiment, the agent is a peptide molecule whose amino acid sequence is derived from a protein binding site on caPCNA.

In an embodiment, the agent is a peptidomimetic molecule whose molecular structure corresponds to a protein binding site on caPCNA.

In an embodiment, the agent is a small molecule that competes with a binding site on caPCNA, wherein the binding site is capable of interacting with the intracellular protein.

A method of selectively inhibiting in vivo interaction of a cancer specific isoform of proliferating cell nuclear antigen (caPCNA) with an intracellular protein in a malignant cell, the method includes the steps of:
  (a) providing an agent that selectively disrupts the interaction of the caPCNA with the intracellular protein, wherein the agent is a peptide or a peptidomimetic, whose amino acid sequence or molecular structure is derived from a caPCNA binding site on the intracellular protein that interacts with the caPCNA;
  (b) administering the agent such that the agent contacts a population of cancer cells in vivo; and
  (c) inhibiting the interaction of caPCNA with the intracellular protein.

A method of reducing in vivo cellular proliferation of malignant cells that express a cancer specific isoform of proliferating cell nuclear antigen (caPCNA), the method includes the steps of:
  (a) providing an agent that selectively disrupts the interaction of the caPCNA with an intracellular protein;
  (b) administering the agent such that the agent contacts a population of cancer cells in vivo; and
  (c) reducing the cellular proliferation of malignant cells.

A method of augmenting cancer therapy for cancers that express a cancer specific isoform of proliferating cell nuclear antigen (caPCNA), the method includes the steps of:
  (a) providing an agent that selectively disrupts the interaction of the caPCNA with an intracellular protein;
  (b) providing a chemotherapeutic agent for cancers;
  (c) administering the agent and the chemotherapeutic agent such that at least a portion of the agents contacts a population of cancer cells in vivo; and
  (d) augmenting cancer therapy, wherein an increased number of cancer cells are killed compared to the number of cancer cells killed by chemotherapy alone.

A method of identifying a candidate agent that selectively inhibits in vivo interaction of a cancer specific isoform of proliferating cell nuclear antigen (caPCNA) with an intracellular protein in a malignant cell, the method includes the steps of:
  (a) providing an agent;
  (b) providing a caPCNA-derived peptide;
  (c) identifying an agent that binds to the caPCNA-derived peptide; and
  (d) determining the agent as the candidate agent, if the candidate agent inhibits the interaction of caPCNA with the intracellular protein.

Rational drug design methodologies can also be implemented to obtain specific inhibitors of caPCNA cellular interaction based on the structural or sequence information of a caPCNA derived peptide, e.g., a peptide that has an amino acid sequence LGIPEQEY (SEQ ID NO: 1). In an embodiment, the agent is a peptide fragment derived from an intracellular protein. In an embodiment, the intracellular protein is known to interact with caPCNA.

A therapeutic composition for reducing in vivo cellular proliferation of malignant cells that express a cancer specific isoform of proliferating cell nuclear antigen (caPCNA), the composition includes a peptide molecule that has an amino acid sequence LGIPEQEY (SEQ ID NO: 1) or a functionally equivalent structure thereof or a peptidomimetic thereof, wherein the peptide molecule is derived from the amino acid sequence of caPCNA. In an embodiment, the peptide molecule further includes a peptide domain that facilitates peptide uptake across cells.

A liposome composition for reducing in vivo cellular proliferation of malignant cells that express a cancer specific isoform of proliferating cell nuclear antigen (caPCNA), the composition includes a peptide molecule comprising an amino acid sequence LGIPEQEY (SEQ ID NO: 1) or a functionally equivalent structure thereof or a peptidomimetic thereof, wherein the peptide molecule is derived from the amino acid sequence of caPCNA.

A recombinant cell that expresses a caPCNA-derived peptide, wherein the peptide selectively disrupts protein-protein interaction in cancer cells. In an embodiment, the caPCNA-derived peptide includes an amino acid sequence LGIPEQEY (SEQ ID NO: 1).

A synthetic peptide that includes an amino acid sequence LGIPEQEY (SEQ ID NO: 1) and a peptide translocation sequence.

A therapeutic composition for reducing cellular proliferation of malignant cells that express a cancer specific isoform of proliferating cell nuclear antigen (caPCNA) including the peptide molecule having an amino acid sequence LGIPEQEY (SEQ ID NO: 1). The peptide molecule is cell permeable, includes a peptide translocation sequence. The peptide is protease resistant. Suitable chemotherapeutic agents that are used along with the peptide inhibitors include doxorubicin, paclitaxel, docetaxel, cisplatin, datrexate, gemcitabine, or vinorelbine or a combination thereof.

Other suitable PCNA-derived peptide inhibitors include VEQLGIPEQEY (SEQ ID NO: 2), LGIPEQEYSCVVK (SEQ ID NO: 3), LGIPEQEYSCVVKMPSG (SEQ ID NO: 4), EQLGIPEQEY (SEQ ID NO: 5), QLGIPEQEY (SEQ ID NO: 6), LGIPEQEYSCVVKMPS (SEQ ID NO: 7), LGIPEQEYSCVVKMP (SEQ ID NO: 8), LGIPEQEYSCVVKM (SEQ ID NO: 9), LGIPEQEYSCVV (SEQ ID NO: 10), LGIPEQEYSCV (SEQ ID NO: 11), LGIPEQEYSC (SEQ ID NO: 12), LGIPEQEYS (SEQ ID NO: 13) and combinations of the additional NH2 and COOH termini amino acids that flank LGIPEQEY (SEQ ID NO: 1).

DETAILED DESCRIPTION

Figure 1:
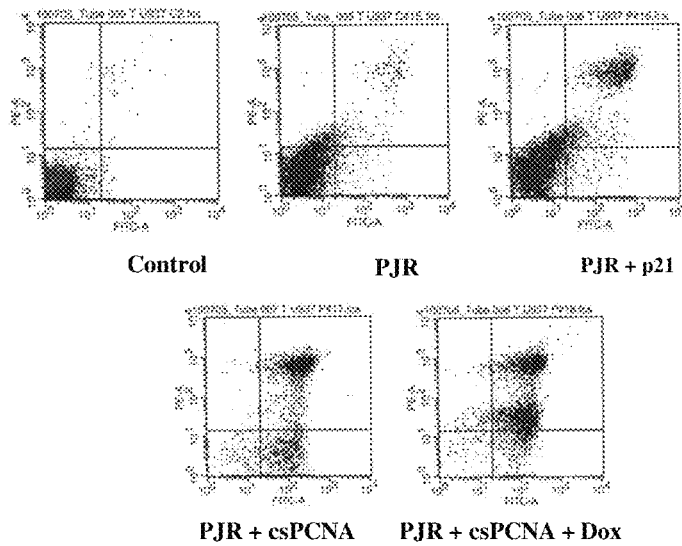
FIG. 1 shows flow-cytometric analysis of caPCNA target peptide sequence transfection experiments with breast cancer cells.

Methods and compositions disclosed herein relate to caPCNA-derived and caPCNA-interacting protein-derived (e.g., p21, XPG, Cdk2) peptides, peptidomimetics, functional analogs thereof and small molecules that selectively disrupt vital cellular functions in cancer cells. There are at least two modes of actions of these peptides. For example, caPCNA-derived peptides either compete with caPCNA to bind to caPCNA-interacting proteins or alternatively bind to a site on caPCNA-interacting protein that disrupts the interaction. caPCNA-interacting protein-derived peptides compete for their corresponding binding site on caPCNA and thereby prevent the caPCNA-interacting proteins to bind to caPCNA.

Specific peptides derived from the caPCNA protein sequence have the ability to block the binding of several cellular proteins that participate in either DNA replication, repair, cell cycle control, apoptosis, transcription, or chromosomal recombination in cancer cells. The binding of caPCNA to these cellular proteins is disrupted when the peptide is allowed to compete with these proteins for their naturally occurring binding site on PCNA. By disrupting the naturally occurring interaction between PCNA and the proteins that bind to or interact with PCNA, normal cellular functions that recruit PCNA are disrupted. This disruption of vital cellular machinery renders the caPCNA-derived peptides cytotoxic by themselves or in combination with other molecules, such as, for example cancer chemotherapeutic drugs. These peptides, either alone or in combination with other cancer therapy agents are useful cancer chemotherapeutics or augmenters of the pharmacodynamic effect of specific anti-cancer chemotherapeutics. These PCNA-derived peptide molecules are also useful as inhibitors of specific cellular processes enabling new mechanistic insights and therapeutic methods to regulate specific cellular functions in both normal and cancer cells that involve PCNA.

In general, peptide inhibitors are based upon the concept that disrupting protein-protein interactions will lead to disruptions in the cellular processes mediated by these protein interactions. However, these peptide inhibitors do not take into account the need to identify a "cancer specific" amino acid sequence that is only available in the cancer cell, but not the non-cancer cell due to the amino acid sequence being "hidden" in the non-cancer cell due to a variety of means such as a post-translational modification, protein conformational shift, binding to a protein that is over-expressed in the cancer cell, or the loss of a binding partner in a cancer cell. Thus the cancer specific nature of the target sequences identified herein are specific in interrupting protein-protein interactions in cancer cells.

Peptide fragments derived from the protein Proliferating Cell Nuclear Antigen (PCNA) are identified herein that have the ability to act, in conjunction with DNA damaging agents (e.g., doxorubicin), to enhance the therapeutic effects of such agents to treat a variety of cancer cells. The peptides are derived from the amino acid sequence within PCNA, for example, encompassing amino acids 126-133. This sequence appears to be uniquely exposed in cancer cells, but not non-cancer cells. By preventing PCNA-binding proteins, including XPG, from binding directly to caPCNA in cancer cells the effects of chemotherapeutic drugs including DNA damaging agents are enhanced. The intrinsic cytotoxicity of the peptide sequence was determined by incubating suitable cells either with the peptide as a single agent or in combination with cytotoxic drugs such as doxorubicin. Exponentially growing U937 leukemia cell cultures in tissue culture media were used. A liposome mediated protein transfer technique was used wherein the caPCNA peptide (126-133) and doxorubicin were encapsulated in liposomes and added to the cell cultures at 10 µM. Using the leukemia cell line U937, the results indicated that the peptide has an intrinsic cytotoxicity, while incubation of the U937 cells with this peptide and a range of concentrations of doxorubicin increased the cytotoxicity of doxorubicin by approximately 3 fold. This approach produced over a 50% killing of the cultured cells within 24 hours that was peptide/drug specific, and not due to liposome mediated cytotoxicity.

As a positive control, these leukemia cells were also incubated for several hours (either 4 or 24 hours) with a peptide derived from the p21waf protein, and as a negative control, a peptide derived from the yeast myosin protein. The results indicated that the p21 peptide was very cytotoxic (>60% kill) even in the absence of doxorubicin, while the PCNA derived peptide (amino acids 126-133) killed approximately 20% of the leukemia cells. Cell killing vs. cell damage was assessed by flow cytometry using propidium iodide and annexin V staining.

These studies indicated that the peptide corresponding to amino acids 126-133 within the PCNA sequence, has anticancer chemotherapeutic activity. In addition, the data indicates that additional peptide sequences within either the PCNA protein, or any of its binding partners, can similarly interfere with the specific cellular processes which regulate cell proliferation and influence cell survival. Peptides from the contact regions between PCNA and proteins with which PCNA interacts are able to disrupt critical cellular processes. For example, additional peptides from the interaction sites of 3 other proteins known to bind to PCNA (i.e., Fen 1, p21, HDAC1), can be designed to have an inhibitory role in critical cellular processes such as DNA replication and cell cycle checkpoint control. These peptides have a cancer specific effect that differentially inhibits cancer cell proliferation, while having little effect on normal cell division. This difference in effect depends, at least in part, on differences within the interaction site between caPCNA and its binding partners becoming structurally altered—a conformational change induced by differences in post-translational modifications between malignant and non-malignant cells). As a therapeutic strategy, alterations in the physical form of the peptides, for example, changing the naturally occurring L-amino acid form to an alternate form, (e.g., switching to the D-amino acid, or altering the peptide bond between individual amino acids so as to reduce non-specific degradation by proteolysis), is a useful method for prolonging the half-life of the peptide, when these modified peptides are used therapeutically.

caPCNA-derived peptides and peptidomimetics represent a novel third generation of anti-cancer therapeutic agents in that these peptides selectively act as competitors of the components that utilize PCNA in the cancer cell. The molecular targets represented by the peptides' amino acid sequences are expressed predominantly in cancer cells. Thus, the peptides disclosed herein represent a significant advance over current second generation therapeutics in that the current second generation therapeutics target a specific pathway that may be either up or down regulated or expressed in the cancer cell. In the case of the second generation agents, these cellular pathways are also active in non-cancer cells and modulation of specific steps within these pathways by these second generation drugs or peptides or agents cannot significantly discriminate between cancer cells and non-cancer cells.

The peptide sequences disclosed herein target a region of the caPCNA protein that is likely to be uniquely unfolded in cancer cells, and these peptides consequently react with a caPCNA selective antibody. Thus, the peptides disclosed herein are designed to selectively target malignant cells by virtue of their ability to compete with caPCNA for regulating the activity of specific proteins interacting with the amino acid sequences within PCNA that are involved in at least one of the following cellular processes: DNA replication, repair, recombination, transcription, cell cycle checkpoint control, and apoptosis.

The peptides disclosed herein are synthesized using standard peptide synthesis procedures and equipments or can be obtained commercially (e.g., United Biochemical Research Co., Seattle, Wash.). A caPCNA-derived peptide that includes amino acids 126-133 of the human PCNA molecule (LGIPEQEY) (SEQ ID NO: 1) followed by an insulin receptor sequence (RYIRS) (SEQ ID NO: 38) to facilitate uptake of the peptide into cells selectively inhibits cancer cells in vitro. Uptake of this peptide was initiated by incubation of this peptide with the cancer cells in the presence of dimethyl sulfoxide (DMSO) in either phosphate buffered saline (PBS) or culture media containing 0.2-2% DMSO, without serum for about 4-24 hours. Uptake of this peptide was also efficiently mediated by encapsulation of the peptide in a liposome formulation and subsequent incubation with the cancer cells at 37° C. for about 4-24 hours. This peptide also augments the cytotoxic effects of chemotherapeutic agents such as doxorubicin.

The term "agent" as used herein includes nucleic acids, proteins, protein fragments, peptides, synthetic peptides, peptidomimetics, analogs thereof, small molecules, inhibitors, and any chemical, organic or bioorganic molecule capable of affecting protein-protein interaction or a cellular process.

The term "caPCNA-derived peptides" and "PCNA-derived peptides" mean peptides, modified peptide sequences with amino acid substitutions or amino acid analogs or amino acid deletions compared to a corresponding region in PCNA, and peptidomimetics that correspond to a particular region in PCNA. The PCNA-derived peptides can range from about 5-50 amino acids in length or about 5-20 amino acids in length or about 5-10 amino acids in length. The PCNA-derived peptides can also include purification tags such as his-tag, FLAG-epitopes, RYIRS tag, and sequences that promote peptide translocation across cellular membranes. The PCNA-derived peptides can also be modified to affect their lipophilicity to enhance peptide delivery into cancer cells. The peptides can be synthesized ("synthetic peptides") or can also be produced through recombinant techniques ("recombinant peptide"). These peptides can also be engineered to increase their in vivo stability without significantly affecting their efficacy in inhibiting caPCNA-protein interactions. Mutations including insertions, deletions, substitutions, amino acid modifications that substantially do not affect the inhibitory activity of the peptides disclosed herein are also included. Peptides that consist essentially of the 126-133 sequence LGIPEQEY (SEQ ID NO: 1) may include other specific or non-specific sequences.

A "peptide derivative" means a molecule having an amino acid sequence of a region of PCNA or of a PCNA homolog, but additionally having at least one chemical modification of one or more of its amino acid side groups, α-carbon atoms, terminal amino group, or terminal carboxylic acid group. A chemical modification includes adding chemical moieties, creating new bonds, and removing chemical moieties. Modifications at amino acid side groups include acylation of lysine, ε-amino groups, N-alkylation of arginine, histidine, or lysine, alkylation of glutamic or aspartic carboxylic acid groups, and deamidation of glutamine or asparagine. Modifications of the terminal amino include the des-amino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a C1-C4 alkyl. Furthermore, one or more side groups, or terminal groups, may be protected by protective groups known to the ordinarily-skilled protein chemist. The α-carbon of an amino acid may be mono- or di-methylated.

The PCNA-derived peptides can also be fused or otherwise linked to a ligand for a cell surface receptor that is present in cancer cells. For example, the human transferrin receptor (hTfR), a marker for cellular proliferation is used as a target for therapeutics and is expressed at least 100-fold more in oral, liver, pancreatic, prostate, and other cancers (Lee et al., (2001) "Receptor mediated uptake of peptides that bind the human transferrin receptor" Eur. J. Biochem., 268: 2004-2012). Peptides, HAIYPRH (SEQ ID NO: 14) and THRPPMWSPVWP (SEQ ID NO: 15) bind specifically hTfR and these peptides were able to target associated macromolecule to the hTfR (Lee, supra). These peptides bind sites that do not overlap with the native ligand, Tf, and are useful in vivo for targeting macromolecules to the endocytic pathway in hTfR-positive cells (Lee, supra). Such peptides can also be used to target PCNA-derived peptides to enhance peptide delivery and also to further enhance specific delivery.

Examples of suitable cell-permeable peptides or peptide domains to link or fuse caPCNA-derived peptides include, for example, small polybasic peptides derived from the transduction domains of certain proteins, such as the third-helix of the Antennapedia (Antp) homeodomain, an RYIRS tag sequence, Penetratin (RQIKIWFQNRRMKWKK) (SEQ ID NO: 16), Tat (GRKKRRQRRRPPQ) (SEQ ID NO: 17), Transportan (GWTLNSAGYLLGKINLKALAALAKKIL) (SEQ ID NO: 18), VP22 (DAATATRGRSAASRPTERPRAPARSASRPRRPVD) (SEQ ID NO: 19), Amphipathic peptides (secondary and primary), MAP (KLALKLALKALKAALKLA) (SEQ ID NO: 20), KALA (WEAKLAKALAKALAKHLAKALAKALKACEA) (SEQ ID NO: 21), ppTG20 (GLFRALLRLLRSLWRLLLRA) (SEQ ID NO: 22), Trimer (VRLPPP) (SEQ ID NO: 23), P1 (MGLGLHLLVLAAALQGAWSQPKKKRKV) (SEQ ID NO: 24), MPG (GALFLGFLGAAGSTMGAWSQP-KKKRKV) (SEQ ID NO: 25), Pep-1 (KETWWETWW-TEWSQPKKKRKV) (SEQ ID NO: 26), hCT (LGTYTQD-FNKFHTFPQTAIGVGAP) (SEQ ID NO: 27), and others.

Specific chemotherapy for cancers include paclitaxel, docetaxel, cisplatin, methotrexate, cyclophosphamide, 5-fluoro uridine, Leucovorin, Irinotecan, Paclitaxel, Carboplatin, doxorubicin, fluorouracil carboplatin, edatrexate, gemcitabine, or vinorelbine or a combination thereof.

The peptides disclosed herein are also suitable for cancer patients undergoing radiotherapy and any other forms of cancer therapy. The peptide inhibitors disclosed herein are suitable augmenting agents that can be administered either prior to, during, and after administering a particular cancer therapy, e.g., chemotherapy or radiotherapy.

It is to be understood that cancers suitable for treatment using the peptides disclosed herein include, but are not limited to, malignancies such as various forms of glioblastoma, glioma, astrocytoma, meningioma, neuroblastoma, retinoblastoma, melanoma, colon carcinoma, lung carcinoma, adenocarcinoma, cervical carcinoma, ovarian carcinoma, bladder carcinoma, lymphoblastoma, leukemia, osteosarcoma, breast carcinoma, hepatoma, nephroma, adrenal carcinoma, or prostate carcinoma, esophageal carcinoma. If a malignant cell expresses csPCNA isoform, the compositions disclosed herein are capable of disrupting the interaction of caPCNA isoform with one or more proteins.

The term "peptidomimetic" or "peptide mimetic" refers to a chemical compound having small protein-like chain (peptide) that includes non-peptidic elements such as non-natural amino acids. Peptidomimetics are designed and synthesized with the purpose of binding to target proteins in order to induce or effect a particular change. Generally, a peptidomimetic functions by mimicking or antagonizing key interactions of the parent peptide structure that it was designed to mimic or antagonize. A peptidomimetic normally does not have classical peptide characteristics such as enzymatically cleavable peptidic bonds. For a general review of the various techniques available for design and synthesis peptide mimetics, see al-Obeidi et al., (1998), "Peptide and peptidomimetic libraries. Molecular diversity and drug design" *Mol Biotechnol.;* 9(3):205-23; and Houben-Weyl: Synthesis of Peptides and Peptidomemetics, Thieme Medical Publishers, 4$^{th}$ edition (2003).

In another embodiment, peptides capable of disrupting ca(cs)PCNA interaction include peptides of amino acid sequences that include about +3 contiguous or non contiguous additional amino acids on the NH$_2$ terminus of LGIPEQEY(SEQ ID NO: 1) and about +9 contiguous or non contiguous amino acids on the COOH terminus of LGIPEQEY(SEQ ID NO: 1). For example, some of these peptides include amino acid sequences of VEQLGIPEQEY (SEQ ID NO: 2) (+3—NH2 terminus), LGIPEQEYSCVVK (SEQ ID NO: 3) (+5—COOH terminus), LGIPEQEYSCV-VKMPSG (SEQ ID NO: 4) (+9—COOH terminus), EQL-GIPEQEY (SEQ ID NO: 5) (+2—NH2 terminus), QLGIPEQEY (SEQ ID NO: 6) (+1—NH2 terminus), LGIPEQEYSCVVKMPS (SEQ ID NO: 7) (+8—COOH terminus), LGIPEQEYSCVVKMP (SEQ ID NO: 8) (+7—COOH terminus), LGIPEQEYSCVVKM (SEQ ID NO: 9) (+6—COOH terminus), LGIPEQEYSCVV (SEQ ID NO: 10) (+4—COOH terminus), LGIPEQEYSCV (SEQ ID NO: 11) (+3—COOH terminus), LGIPEQEYSC (SEQ ID NO: 12) (+2—COOH terminus), LGIPEQEYS (SEQ ID NO: 13) (+1—COOH terminus) and combinations of the additional NH2 and COOH termini amino acids that flank LGIPEQEY (SEQ ID NO: 1). Amino acid mutations including substitutions that do not affect the specificity of the peptides to generate csPCNA specific antibodies are within the scope of this disclosure. One or more of the amino acid residues in the peptides may be replaced with an amino acid analog or an unnatural amino acid. In addition, peptide mimetics developed based on the sequences of the peptides disclosed herein, can also be used to generate antibodies to csPCNA isoform.

Dosage of the PCNA-derived peptides and other PCNA-interacting protein-derived peptides depend on the efficacy of the peptides, stability of the peptides in vivo, mode of administration, the nature of cancer being treated, body weight, age of the patient and other factors that are commonly considered by a skilled artisan. For example, dosage of a PCNA-derived peptide drug can range from about 0.1-10.0 microgram (mcg)/kg body weight or from about 0.2-1.0 mcg/kg body weight or from about 0.5-5.0 mcg/kg body weight or from about 10.0-50.0 mcg/kg body weight. Depending on the toxicity effects and tumor killing capability, the dosage can also range from about 1.0-10.0 mg/kg body weight and from about 0.1-1.0 mg/kg body weight.

Administration of the compositions disclosed herein may be via any route known to be effective by the physician of ordinary skill. Peripheral, parenteral administrations are suitable. Parenteral administration is commonly understood in the medical literature as the injection of a dosage form into the body by a sterile syringe. Peripheral parenteral routes include intravenous, intramuscular, subcutaneous, and intraperitoneal routes of administration. Intravenous, intramuscular, and subcutaneous routes of administration of the compositions disclosed herein are suitable. For parenteral administration, the peptides disclosed herein can be combined with phosphate buffered saline (PBS) or any suitable pyrogen-free pharmaceutical grade buffer that meets FDA standard for human subject administration. As used herein, "pharmaceutically acceptable carrier" includes any and all solvents, diluents, or other liquid vehicle, dispersion or suspension aids, surface active agents, isotonic agents, thickening or emulsifying agents, preservatives and the like, as suited to the particular dosage form desired. Remington's Pharmaceutical Sciences, 20$^{th}$ Edition, A. R. Gennaro (Williams and Wilkins, Baltimore, Md., 2000) discloses various carriers used in formulating pharmaceutical compositions and known techniques for the preparation thereof. Solutions or suspensions of the compositions described herein can also include a sterile diluent, such as water for injection, saline solution, fixed oils, polyethylene glycols, glycerine, propyleneglycol or other synthetic solvents; chelating agents, such as EDTA; buffers, such as acetates, citrates or phosphates; and agents for the adjustment of tonicity, such as sodium chloride or dextrose. A parenteral preparation of the compositions can be enclosed in ampoules, disposable syringes or multiple dose vials made of glass or plastic, in accordance with standard practice in the field. The compositions disclosed herein can be stored as a lyophilized sterile powder in vials containing for reconstitution and the unreconstituted product may be stored at −20° C.

Peptides and other compositions disclosed herein can be administered via any suitable means. For example, the peptide compositions may be diluted in saline or any suitable buffer and administered directly intravenously. For example, the peptide compositions can be encapsulated in liposomes and administered intravenously of by any suitable method. For example, the peptide compositions can be delivered by an extended release drug delivery system known to one of ordinary skill in the art. Other modes of targeting tumors are also suitable. For example, U.S. patent application publication US20050008572 (Prokop et al.,) discloses methods and compositions relating to nanoparticular tumor targeting and therapy, the disclosure of which is hereby incorporated by reference. U.S. patent application publication US20030212031 (Huang et al.,) discloses stable lipid-comprising drug delivery complexes and methods for their production, the disclosure of which is hereby incorporated by reference.

EXAMPLE 1

Cytotoxic Effects of a caPCNA-Derived Peptide on Breast Cancer Cells

Exponentially growing breast cancer cells were grown in culture media to 50% of confluence (FIG. 1). The media was then changed and liposomes that were prepared from transfection reagent (PJR) were incubated with the cells in fresh media for an additional 24 hours prior to performing flow-cytometric analysis of the treated cells.

Liposomes contained either the carboxyl region of the p21waf1 protein, and/or the caPCNA antigenic site peptide (LGIPEQEY) (SEQ ID NO: 1). After 24 hours, the cells were stained with propidium iodide and fluorescently labeled annexin V antibody. Healthy growing cells were not permeable to the antibody as shown in lower left panel of FIG. 1, while permeabilized healthy cells susceptible to the transfection reagent, but still growing, were stained with propidium iodide. Cells staining with the annexin V antibody indicate some level of damage associated with the induction of apoptotic cells (lower right quadrant, FIG. 1), and/or cells that had died from either apoptosis or necrosis (upper right quadrant, FIG. 1). These results demonstrate that control cells treated with saline produced a flow profile associated with the 1$^{st}$ upper left panel (FIG. 1). Cells treated with only the transfection reagent slightly affected the condition of the cells and lead to a slight increase in the number of apoptotic and necrotic cells. Cells treated with the p21 cytotoxic peptide fragment exhibited induced cell killing (upper right panel, FIG. 1), and cells treated with the caPCNA peptide showed a strong cytotoxic response and most of the healthy growing cells were damaged and were in the process of undergoing either apoptosis or cell death. Combining the caPCNA peptide with 100 µM doxorubicin resulted in almost 90% cell killing within the measured time period. In addition, approximately 5-7% of the remaining cells appeared to be undergoing apoptosis and was slated to die. Cells treated with low doses of doxorubicin led to a significant level of cell killing, and combining the caPCNA peptide with this dosage of doxorubicin led to a synergistic effect that resulted in the death of almost all of the cells that were analyzed. At sub lethal concentrations of this drug, exposure of the cells to a set of low concentrations of the peptide significantly enhances the lethality of doxorubicin.

EXAMPLE 2

XPG-GST Fusion Protein Preferentially Binds to caPCNA Compared to nmPCNA

Figure 2:
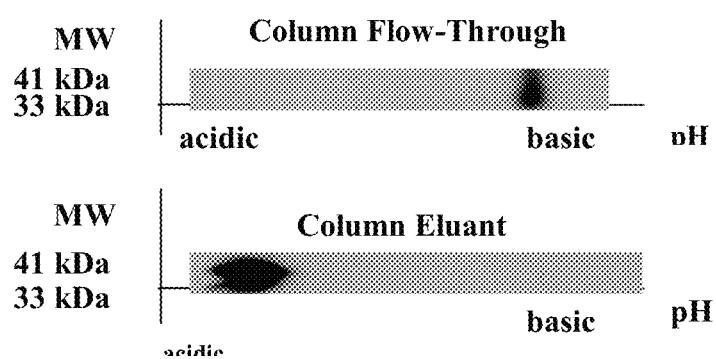
FIG. 2 shows 2D-PAGE analysis of XPG-GST affinity column fractions for PCNA.
Figure 3:
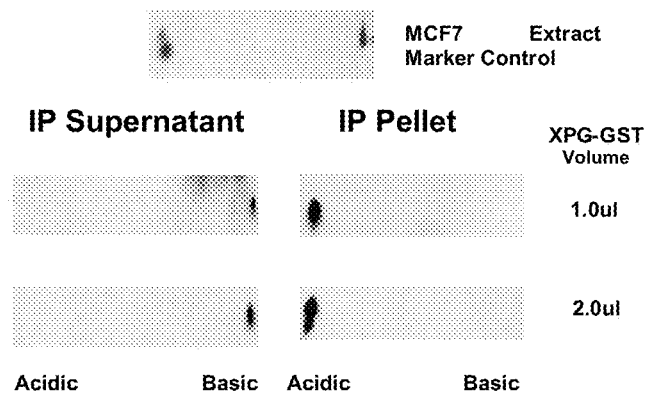
FIG. 3 shows XPG-GST fusion protein specifically immunoprecipitates caPCNA. Thirty μg aliquots of MCF7 cell extract were treated as described in the text. The PC10 antibody used to visualize PCNA in the Western blot analysis was used at a dilution of 1:1000.

Earlier attempts to selectively isolate and purify caPCNA were unsuccessful. This problem was overcome by using an immobilized XPG-GST fusion protein system as an affinity matrix for caPCNA purification (FIG. 2). Commonly used techniques to purify PCNA that employ chromatography steps on phosphocellulose, phenyl Sepharose, and Q-Sepharose matrices resulted in the presence of the two isoforms together in the protein fraction. To separate the two PCNA isoforms, immobilized XPG-GST fusion protein fragment was incorporated into the affinity column containing into the purification scheme (FIG. 3). Because of the differential binding affinities of the XPG portion of the fusion protein for the two isoforms of PCNA, this methodology resulted in an effective purification of caPCNA from nmPCNA. Subsequent 2D-PAGE analysis of the flow-through and eluant from the affinity (XPG-GST) column demonstrated that the basic PCNA isoform present in non-malignant cells, (nmPCNA), is found in the flow-through of the affinity column, while the acidic (caPCNA) isoform was recovered in a fraction eluted from the column (FIG. 2).

MCF7 cell (human breast adenocarcinoma cell line) extracts were processed for purification of the synthesome. MCF7 derived synthesome was then subjected to chromatography steps on phosphocellulose, phenyl Sepharose, and Q-Sepharose matrices as described in (Malkas, L. and Hickey, R. (1996) The expression, purification and characterization of DNA polymerases involved in papovavirus replication. In: *Methods in Enzymol* Vol. 275: Viral Polymerases and Related Proteins, Acad. Press (133-167).). The Q-Sepharose eluted fraction containing both the nmPCNA and caPCNA isoforms was then loaded onto a XPG-GST affinity column. The column was eluted and both the column flow-through and eluate were subjected to 2D-PAGE Western blot analysis using PC10 antibody. The PC10 antibody was used at a dilution of 1:1000 in the Western blot analysis.

caPCNA was specifically immunoprecipitated from a MCF7 cell extract using XPG-GST fusion protein (FIG. 3). Thirty microgram samples of MCF7 cell extract were incubated with XPG-GST fusion protein for two hours, followed by incubation with Glutathione agarose beads for one hour to capture the XPG-GST. The mixture was then centrifuged to collect the beads, and the supernatant and the agarose bead pellet containing the XPG-GST PCNA complex were subjected to 2D-PAGE Western blot analysis. The Western blots were then probed using commercially available PC10 antibody. As can be seen in FIG. 3, XPG-GST was readily able to recognize and precipitate caPCNA selectively from the MCF7 breast cancer cell extract, leaving the nmPCNA isoform in the supernatant fraction.

Example 1 describes the effect of a caPCNA-derived peptide on the cytotoxicity of cancer cells. The caPCNA-derived peptide site on caPCNA serves as a molecular lock into which any of a variety of key proteins fit, for example XGP (Xeroderma Pigmentosum G protein). These interacting proteins serve as keys that activate specific cellular process such as DNA repair, cell cycle checkpoint regulation, and the like, when they interact with PCNA. The therapeutic benefit achieved by disrupting the binding of these proteins to PCNA relates to the difference in the structure of this binding site between the cancer specific and normal cell isoforms of PCNA, as demonstrated by the preferential binding of the immobilized XPG-GST fusion protein fragment to caPCNA. The cancer cell is sensitive to such disruption since the binding site is exposed on caPCNA, but is hidden in the nmPCNA isoform. This binding site is unavailable or not accessible when the competing peptide is present, or the binding site has an affinity for the binding protein that differs between the malignant and non-malignant cell types.

Figure 4:
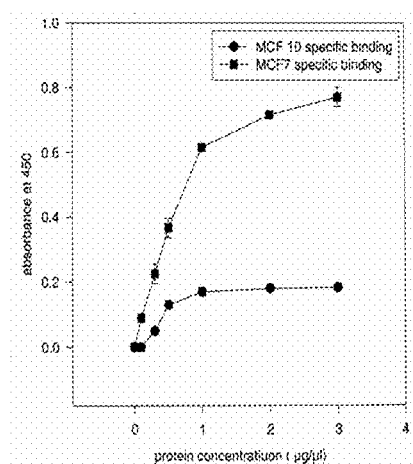
FIG. 4 shows results from an ELISA method for the detection of caPCNA.

Use of the "keys" binding to the caPCNA "lock", i.e., regions or domains or epitopes within the interacting intracellular proteins can also be used as potential therapeutics and potential therapeutic targets. Evidence for the selective binding of one of these proteins to this site on caPCNA is demonstrated in the form of a fragment of the XPG protein fused to the glutathione-S-transferase gene product (i.e., GST)) as provided in FIGS. 2-4. The rationale for this methodology is based upon the observation that a peptidomimetic (based upon the antigenic site of caPCNA) is capable of enhancing cancer cell killing by doxorubicin. This likely occurs either because the peptide corresponding to this antigenic site directly competes with caPCNA for the proteins binding to caPCNA, or binds to one or more of the specific proteins interacting with PCNA, through this binding site (aa 126-133 of caPCNA), prior to their association with caPCNA. In either scenario, the peptide prevents association of one or more of these proteins with its complementary binding site on caPCNA. This competition or differential binding in turn disrupts specific cellular processes mediated by this protein-protein interaction, for example, the nucleotide excision repair pathway. FIG. 2 demonstrates that the cancer specific isoform of PCNA (caPCNA) selectively binds to an affinity column prepared by coupling the 29 amino acid fragment of the XPG protein to Glutathione-S-transferase, and expressing the fusion protein in bacteria. The affinity column binds caPCNA under appropriate binding conditions. Elution of the bound caPCNA is achieved by reducing the concentration of NaCl in the buffer from 300 mM to zero mM. This data demonstrates that the XPG-PCNA interaction can be used to selectively bind the caPCNA isoform. FIG. 3 provides further evidence for the specific binding of caPCNA to the XPG fragment expressed as part of the XPG-GST fusion product. The data demonstrate that the XPG-GST protein is used to selectively bind to and precipitate only the caPCNA isoform, while allowing the nmPCNA isoform to remain in solution. Subsequent analysis, by 2D-PAGE, of the proteins selectively bound by the immobilized XPG-GST fusion protein, followed by Western blotting with PCNA selective antibody, demonstrated that the cancer specific isoform of PCNA (acidic) was specifically bound to the immobilized XPG-GST fusion protein; while leaving the nmPCNA isoform unbound and in solution. FIG. 4 indicates that the XPG-GST fusion protein could be used as the primary reagent leading to capture and quantification of caPCNA present in tissue extracts. ELISA results shows that XPG-GST captures caPCNA from cell extracts, and potentially from patient sera samples, if present, and enables the efficient monitoring of caPCNA expressed by individuals with cancer or individuals undergoing treatment for cancer.

These caPCNA-derived and caPCNA-interacting proteins-derived specific proteins and peptide fragments are useful diagnostic tools as well as valuable therapeutic agents. In addition, these peptide fragments also disrupt cell growth and cancer cell proliferation by disrupting protein-protein interactions with the antigenic site on caPCNA e.g., amino acid 126-133.

EXAMPLE 3

Development of an XPG-GST Fusion Protein Based ELISA Assay for the Detection of caPCNA An ELISA assay using the XPG-GST fusion protein was developed to detect the abundance of caPCNA in complex protein mixtures (FIG. 4). XPG-GST fusion protein was bound to ELISA plate wells, and increasing amounts of protein extracts from either malignant MCF7 cells or non-malignant MCF10A breast cells were added to individual sets of wells. Residual binding sites in each well were blocked by incubation with 3% BSA, followed by extensive washing with buffered saline. The commercially available C20 anti-PCNA antibody was used as the primary antibody, and following washing with phosphate buffered saline, each well was incubated with anti-goat IgG conjugated to horseradish peroxidase. Non-specifically bound secondary antibody was removed by washing each well with phosphate buffered saline containing 0.05% Tween 20 detergent and each well was incubated with a buffer containing ABTS [2,2'-Azino-bis [3-ethylbenziazoline-6-sulfonic acid] for 30 minutes before reading the absorbance of the solution at 405 nm. MCF10A cell extracts containing only nmPCNA produced a low level of ABTS conversion to a colored product that saturated at less than 1 μg/ml of extract. In contrast, the ELISA reaction containing MCF7 cell extract, containing both caPCNA and nmPCNA (Bechtel, supra) produced 3 times more colored product at the same concentration of extract, and did not reach saturation even with 3 times more cell extract in the reaction. The difference in absorbance between the reactions containing MCF10A and MCF7 cell extracts represents the amount of caPCNA present in the MCF7 cell extract.

EXAMPLE 4

Specificity of the Interaction of PCNA 126-133 Peptide

Figure 5:
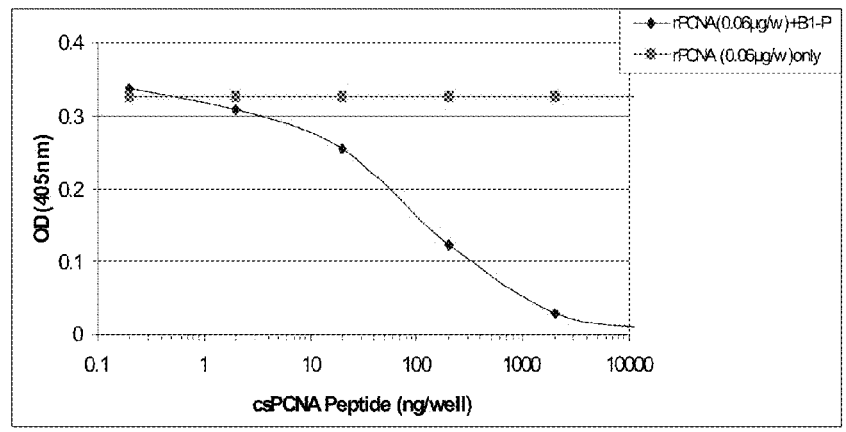
FIG. 5 shows the results of an ELISA in which caPCNA antibody (caPCNAab) is bound to the plate and being used to capture the isolated caPCNA. The wells are washed and then incubated with a goat anti-PCNA antibody (C20) that recognizes the C-terminal 20 amino acids of PCNA. Bound C20 antibody is visualized with an alkaline phosphatase conjugated anti-goat IgG antibody, and bound antibody complex is visualized with p-nitrophenol phosphate, and quantified by spectrophotometry. The competition experiments shown in this study involve the simultaneous incubation of the ca(cs) PCNA with increasing amounts of the antigenic peptide fragment of caPCNA (referred to as B1 or the PCNA aa126-133 peptide) in this assay. Reduction in binding of the caPCNA whole molecule in the presence of increasing concentrations of peptide B1 are shown, and demonstrate that the ELISA assay is specific for recognition of the caPCNA epitope defined by this peptide sequence.

FIG. 5 shows the results of an ELISA in which caPCNAab is bound to the plate and being used to capture the isolated caPCNA. The wells are washed and then incubated with a goat anti-PCNA antibody (C20) that recognizes the C-terminal 20 amino acids of PCNA. Bound C20 antibody is visualized with an alkaline phosphatase conjugated anti-goat IgG antibody, and bound antibody complex is visualized with p-nitrophenol phosphate, and quantified by spectrophotometry. The competition experiments shown in this study involve the simultaneous incubation of the ca(cs)PCNA with increasing amounts of the antigenic peptide fragment of caPCNA (referred to as B1 or the PCNA aa126-133 peptide) in this assay. Reduction in binding of the caPCNA whole molecule in the presence of increasing concentrations of peptide B1 are shown, and demonstrate that the ELISA assay is specific for recognition of the caPCNA epitope defined by this peptide sequence.

Figure 6:
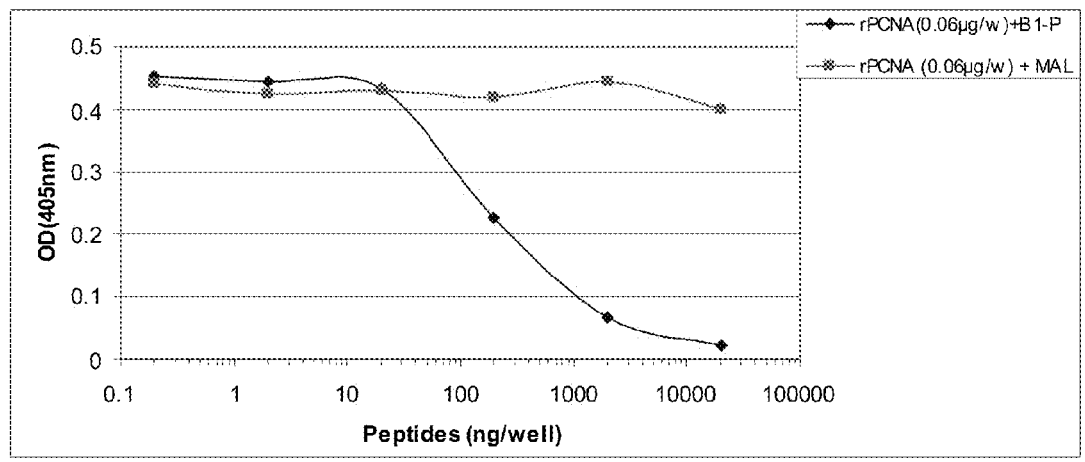
FIG. 6 shows the specificity of the peptide sequence as the epitope recognized by the caPCNA antibody.

The assay described in FIG. 5 was used to test the specificity of the antibody combining site for the epitope defined by PCNA aa126-133 (FIG. 6). The ELISA assay was performed as described in aim 1, however, either the B1 peptide or a peptide sequence (H-Ser-Ala-Cys-Glu-Gln-Ile-Leu-Lys-Asp-Thr-OH) (SEQ ID NO: 28) taken from within the yeast myosin protein was used to compete for the antibody in the presence of purified caPCNA. As shown in FIG. 5, the B1 peptide efficiently competes for the antibody combining site, while the unrelated yeast myosin peptide (MAL4) does not compete with caPCNA for binding to the caPCNAab, and does not diminish the amount of PCNA bound to the immobilized caPCNAab bound to the plate. These data demonstrate the specificity of the antibody combining site for the epitope on caPCNA that is defined by the B1 peptide.

Figure 7:
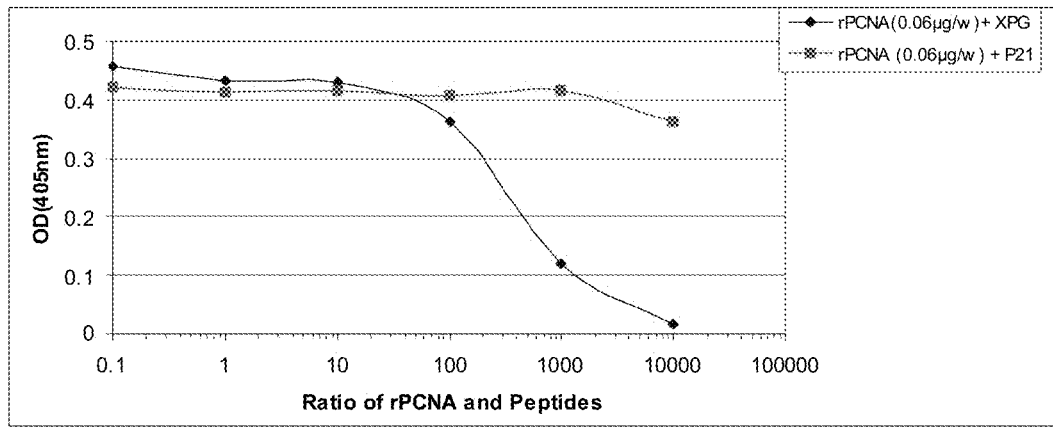
FIG. 7 illustrates the interaction of the XPG-PCNA interaction domain. The ELISA assay described herein was utilized to evaluate whether the B1 peptide (PCNA aa126-133) could interact directly with XPG at the defined PCNA-XPG interaction domain.

The ELISA described herein was used to monitor the ability of two peptides to disrupt caPCNA binding to the bound caPCNA antibody. One peptide (H-Gly-Arg-Lys-Arg-Arg-Gln-Thr-Ser-Met-Thr-Asp-Arg-Tyr-His-Ser-Lys-Arg-Arg-Leu-Ile-Phe-Ser-OH) (SEQ ID NO: 29) corresponding to the p21cip/waf1 proteins site of interaction with PCNA was evaluated in this assay, and is shown to have no effect on the binding of caPCNA to the bound caPCNA antibody in this ELISA assay (FIG. 7). The other peptide (H-Gln-Thr-Gln-Leu-Arg-Ile-Asp-Ser-Phe-Phe-Arg-OH) (SEQ ID NO: 30) corresponding to the XPG-PCNA interaction site of the XPG protein effectively competed with the purified caPCNA for binding to the cPCNA antibody, and significantly reduced the generation of colored substrate in the assay in direct proportion to the amount of XPG peptide used in this competition assay. The XPG peptide does not in itself interact with the caPCNA antibody, as it is unrelated to the antigenic peptide. Therefore, the XPG peptide interacts with its recognized PCNA binding site in order to block binding of the PCNA protein to the caPCNA antibody. This happens if the epitope recognized by the antibody was masked by specifically binding this XPG peptide. This data indicates that both the caPCNA peptide (aa126-133) and peptides which interact with specific sites within PCNA, such as the XPG peptide and other know PCNA binding partners, could disrupt recognition of PCNA by its regular binding partners and potentially disrupt cellular functions dependent upon these protein-protein interactions.

EXAMPLE 5

Figure 8:
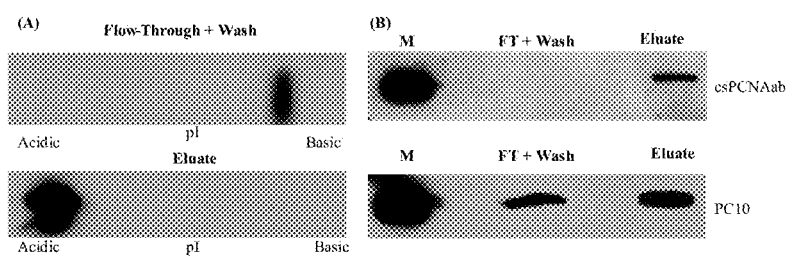
FIG. 8 shows that csPCNA specifically binds XPG. MCF7 cell nuclear extract was prepared, dialyzed into low salt buffer and loaded onto a XPG-GST agarose column pre-equilibrated in low salt buffer conditions. The column was washed with 6 column volumes of pre-equilibration buffer. The column flow through & wash fractions were collected as 1 fraction. The column was eluted using buffer & salt conditions. (A) 2D-PAGE Western blot using PC10 antibody of the XPG-GST agarose column fractions. The PC10 antibody was used at a dilution of 1:1000 in the Western analysis. (B) 1D-PAGE Western analysis using PC10 and csPCNAab antibodies of XPG-GST agarose column fractions. PC10 and csPCNAab antibodies were used at a dilution of 1:1000 in the Western analysis. M denotes the marker.

Functional Differences Between the PCNA Isoforms Part II: XPG Specifically Binds csPCNA A XPG-GST agarose column was prepared and subsequently resolved a MCF7 breast cancer cell nuclear extract using the column. The column flow through, column wash, and eluate conditions were used based on the XPG-PCNA binding conditions. 2D-PAGE analysis of the flow-through+wash and eluant protein fractions from the affinity (XPG-GST) column showed that the basic isoform of PCNA present in non-malignant cells (nmPCNA) was found in the XPG-GST agarose column flow-through+wash fraction, while the acidic PCNA isoform, csPCNA, was recovered in the eluant protein fraction from the column (FIG. 8A). A 1D-PAGE Western analysis of the XPG-GST column fractions was performed using both the PC10 and csPCNAab antibodies (FIG. 8B). It showed that csPCNAab only recognized the PCNA isoform contained in the XPG-GST agarose column eluant fraction suggesting that XPG preferentially binds csPCNA under conditions used to resolve the column, and that the PCNA isoforms have different affinities for known PCNA binding partners.

TABLE 1

Peptide domains containing the PCNA aa 126-133 region.

| |
|---|
| PCNA Sequence 111-125<br>LVFEAPNQEK VSDYEMKLMD LDVEQ<br>(SEQ ID NO: 32) |
| LGIPEQEYSCVVKMP SGEFARICRD LSHIGDAVVI<br>SCAKDGVKFS ASGELGNGNI KLSQTSNVDK EEEAVTIEMN<br>(SEQ ID NO: 31) |
| PCNA Sequence 118-135<br>LVFEAPNQEK VSDYEMKLMD LDVEQLGIPEQEYSC<br>(SEQ ID NO: 33) |

TABLE 1-continued

Peptide domains containing the PCNA aa 126-133 region.

```
VVKMP SGEFARICRD LSHIGDAVVI
SCAKDGVKFS ASGELGNGNI KLSQTSNVDK EEEAVTIEMN

PCNA Sequence 121-133
LVFEAPNQEK VSDYEMKLMD LDVEQLGIPEQEY
(SEQ ID NO: 34)
SCVVKMP SGEFARICRD LSHIGDAVVI
SCAKDGVKFS ASGELGNGNI KLSQTSNVDK EEEAVTIEMN PCNA Sequence 126-133
LVFEAPNQEK VSDYEMKLMD LDVEQLGIPEQEY
(SEQ ID NO: 1)
SCVVKMP SGEFARICRD LSHIGDAVVI
SCAKDGVKFS ASGELGNGNI KLSQTSNVDK EEEAVTIEMN PCNA Sequence 126-143
LVFEAPNQEK VSDYEMKLMD LDVEQLGIPEQEYSCVVKMP SGE
(SEQ ID NO: 35)
```

TABLE 1-continued

Peptide domains containing the PCNA aa 126-133 region.

```
FARICRD LSHIGDAVVI
SCAKDGVKFS ASGELGNGNI KLSQTSNVDK EEEAVTIEMN

PCNA Sequence 126-153
LVFEAPNQEK VSDYEMKLMD LDVEQLGIPEQEYSCVVKMP
SGEFARICRD LSH
(SEQ ID NO: 36)
IGDAVVI
SCAKDGVKFS ASGELGNGNI KLSQTSNVDK EEEAVTIEMN PCNA Sequence 126-163
LVFEAPNQEK VSDYEMKLMD LDVEQLGIPEQEYSCVVKMP
SGEFARICRD LSHIGDAVVI SCA
(SEQ ID NO: 37)
KDGVKFS ASGELGNGNI KLSQTSNVDK EEEAVTIEMN
```

The regions containing the 126-133 domain are shown as underlined.

---

We claim:

1. A therapeutic composition for reducing cellular proliferation of malignant cells that express a cancer specific isoform of proliferating cell nuclear antigen (caPCNA), the composition comprising a peptide molecule selected from the group consisting of:
   a) peptide consisting of the amino acid sequence LGIPEQEY (SEQ ID No. 1) and
   b) peptide comprising the amino acid sequence LGIPEQEY (SEQ ID No. 1) and up to three additional amino acids on the NH2 terminus of LGIPEQEY (SEQ ID No. 1) or up to nine amino acids on the —COOH terminus of LGIPEQEY (SEQ ID No. 1);
   wherein the therapeutic composition further comprises a cell-permeable peptide.

2. The therapeutic composition of claim 1, wherein the cell-permeable peptide is selected from the group consisting of: Antennapedia (Antp) homeodomain, an RYIRS tag sequence, Penetratin (RQIKIWFQNRRMKWKK) (SEQ ID No. 16), Tat (GRKKRRQRRRPPQ) (SEQ ID No. 17), Transportan (GWTLNSAGYLLGKINLKALAALAKKIL) (SEQ ID No. 18), VP22 (DAATATRGRSAASRPTERPRAPARSASRPRRPVD) (SEQ ID No. 19), Amphipathic peptides (secondary and primary), MAP (KLALKLALKALKAALKLA) (SEQ ID No. 20), KALA (WEAKLAKALAKALAKHLAKALAKALKACEA) (SEQ ID No. 21), ppTG20 (GLFRALLRLLRSLWRLLLRA) (SEQ ID No. 22), Trimer (VRLPPP) (SEQ ID No. 23), P1 (MGLGLHLLVLAAALQGAWSQPKKKRKV) (SEQ ID No. 24), MPG (GALFLGFLGAAGSTMGAWSQPKKKRKV) (SEQ ID No. 25), Pep-1 (KETWWETWWTEWSQPKKKRKV) (SEQ ID No. 26), and hCT (LGTYTQDFNKFHTFPQTAIGVGAP) (SEQ ID No. 27).

* * * * *

SEQUENCE LISTING

```
<160> NUMBER OF SEQ ID NOS: 38

<210> SEQ ID NO 1
<211> LENGTH: 8
<212> TYPE: PRT
<213> ORGANISM: artificial
<220> FEATURE:
<223> OTHER INFORMATION: synthetic

<400> SEQUENCE: 1

Leu Gly Ile Pro Glu Gln Glu Tyr
1               5

<210> SEQ ID NO 2
<211> LENGTH: 11
<212> TYPE: PRT
<213> ORGANISM: artificial
<220> FEATURE:
<223> OTHER INFORMATION: synthetic

<400> SEQUENCE: 2

Val Glu Gln Leu Gly Ile Pro Glu Gln Glu Tyr
1               5                   10

<210> SEQ ID NO 3
<211> LENGTH: 13
<212> TYPE: PRT
<213> ORGANISM: Artificial
<220> FEATURE:
<223> OTHER INFORMATION: Synthetic

<400> SEQUENCE: 3

Leu Gly Ile Pro Glu Gln Glu Tyr Ser Cys Val Val Lys
1               5                   10

<210> SEQ ID NO 4
<211> LENGTH: 17
<212> TYPE: PRT
<213> ORGANISM: Artificial
<220> FEATURE:
<223> OTHER INFORMATION: Synthetic

<400> SEQUENCE: 4

Leu Gly Ile Pro Glu Gln Glu Tyr Ser Cys Val Val Lys Met Pro Ser
1               5                   10                  15
```

Gly

<210> SEQ ID NO 5
<211> LENGTH: 10
<212> TYPE: PRT
<213> ORGANISM: Artificial
<220> FEATURE:
<223> OTHER INFORMATION: Synthetic

<400> SEQUENCE: 5

Glu Gln Leu Gly Ile Pro Glu Gln Glu Tyr
1               5                   10

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

Gln Leu Gly Ile Pro Glu Gln Glu Tyr
1               5

<210> SEQ ID NO 7
<211> LENGTH: 16
<212> TYPE: PRT
<213> ORGANISM: Artificial
<220> FEATURE:
<223> OTHER INFORMATION: Synthetic

<400> SEQUENCE: 7

Leu Gly Ile Pro Glu Gln Glu Tyr Ser Cys Val Val Lys Met Pro Ser
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic

<400> SEQUENCE: 8

Leu Gly Ile Pro Glu Gln Glu Tyr Ser Cys Val Val Lys Met Pro
1               5                   10                  15

<210> SEQ ID NO 9
<211> LENGTH: 14
<212> TYPE: PRT
<213> ORGANISM: Artificial
<220> FEATURE:
<223> OTHER INFORMATION: Synthetic

<400> SEQUENCE: 9

Leu Gly Ile Pro Glu Gln Glu Tyr Ser Cys Val Val Lys Met
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic

<400> SEQUENCE: 10

Leu Gly Ile Pro Glu Gln Glu Tyr Ser Cys Val Val

```
<210> SEQ ID NO 11
<211> LENGTH: 11
<212> TYPE: PRT
<213> ORGANISM: Artificial
<220> FEATURE:
<223> OTHER INFORMATION: Synthetic

<400> SEQUENCE: 11

Leu Gly Ile Pro Glu Gln Glu Tyr Ser Cys Val
1               5                   10

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

Leu Gly Ile Pro Glu Gln Glu Tyr Ser Cys
1               5                   10

<210> SEQ ID NO 13
<211> LENGTH: 9
<212> TYPE: PRT
<213> ORGANISM: Artificial
<220> FEATURE:
<223> OTHER INFORMATION: Synthetic

<400> SEQUENCE: 13

Leu Gly Ile Pro Glu Gln Glu Tyr Ser
1               5

<210> SEQ ID NO 14
<211> LENGTH: 7
<212> TYPE: PRT
<213> ORGANISM: Artificial
<220> FEATURE:
<223> OTHER INFORMATION: Synthetic

<400> SEQUENCE: 14

His Ala Ile Tyr Pro Arg His
1               5

<210> SEQ ID NO 15
<211> LENGTH: 12
<212> TYPE: PRT
<213> ORGANISM: Artificial
<220> FEATURE:
<223> OTHER INFORMATION: Synthetic

<400> SEQUENCE: 15

Thr His Arg Pro Pro Met Trp Ser Pro Val Trp Pro
1               5                   10

<210> SEQ ID NO 16
<211> LENGTH: 16
<212> TYPE: PRT
<213> ORGANISM: Artificial
<220> FEATURE:
<223> OTHER INFORMATION: Synthetic

<400> SEQUENCE: 16

Arg Gln Ile Lys Ile Trp Phe Gln Asn Arg Arg Met Lys Trp Lys Lys
1               5                   10                  15
```

```
<210> SEQ ID NO 17
<211> LENGTH: 13
<212> TYPE: PRT
<213> ORGANISM: Artificial
<220> FEATURE:
<223> OTHER INFORMATION: Synthetic

<400> SEQUENCE: 17

Gly Arg Lys Lys Arg Arg Gln Arg Arg Pro Pro Gln
1               5                   10

<210> SEQ ID NO 18
<211> LENGTH: 27
<212> TYPE: PRT
<213> ORGANISM: Artificial
<220> FEATURE:
<223> OTHER INFORMATION: Synthetic

<400> SEQUENCE: 18

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 19
<211> LENGTH: 34
<212> TYPE: PRT
<213> ORGANISM: Artificial
<220> FEATURE:
<223> OTHER INFORMATION: Synthetic

<400> SEQUENCE: 19

Asp Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 20
<211> LENGTH: 18
<212> TYPE: PRT
<213> ORGANISM: Artificial
<220> FEATURE:
<223> OTHER INFORMATION: Synthetic

<400> SEQUENCE: 20

Lys Leu Ala Leu Lys Leu Ala Leu Lys Ala Leu Lys Ala Ala Leu Lys
1               5                   10                  15

Leu Ala

<210> SEQ ID NO 21
<211> LENGTH: 30
<212> TYPE: PRT
<213> ORGANISM: Artificial
<220> FEATURE:
<223> OTHER INFORMATION: Synthetic

<400> SEQUENCE: 21

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30
```

<210> SEQ ID NO 22
<211> LENGTH: 20
<212> TYPE: PRT
<213> ORGANISM: Artificial
<220> FEATURE:
<223> OTHER INFORMATION: Synthetic

<400> SEQUENCE: 22

```
Gly Leu Phe Arg Ala Leu Leu Arg Leu Leu Arg Ser Leu Trp Arg Leu
1               5                   10                  15

Leu Leu Arg Ala
            20
```

<210> SEQ ID NO 23
<211> LENGTH: 6
<212> TYPE: PRT
<213> ORGANISM: Artificial
<220> FEATURE:
<223> OTHER INFORMATION: Synthetic

<400> SEQUENCE: 23

```
Val Arg Leu Pro Pro Pro
1               5
```

<210> SEQ ID NO 24
<211> LENGTH: 27
<212> TYPE: PRT
<213> ORGANISM: Artificial
<220> FEATURE:
<223> OTHER INFORMATION: Synthetic

<400> SEQUENCE: 24

```
Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25
```

<210> SEQ ID NO 25
<211> LENGTH: 27
<212> TYPE: PRT
<213> ORGANISM: Artificial
<220> FEATURE:
<223> OTHER INFORMATION: Synthetic

<400> SEQUENCE: 25

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25
```

<210> SEQ ID NO 26
<211> LENGTH: 21
<212> TYPE: PRT
<213> ORGANISM: Artificial
<220> FEATURE:
<223> OTHER INFORMATION: Synthetic

<400> SEQUENCE: 26

```
Lys Glu Thr Trp Trp Glu Thr Trp Trp Thr Glu Trp Ser Gln Pro Lys
1               5                   10                  15

Lys Lys Arg Lys Val
            20
```

<210> SEQ ID NO 27

```
<211> LENGTH: 24
<212> TYPE: PRT
<213> ORGANISM: Artificial
<220> FEATURE:
<223> OTHER INFORMATION: Synthetic

<400> SEQUENCE: 27

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 28
<211> LENGTH: 10
<212> TYPE: PRT
<213> ORGANISM: Artificial
<220> FEATURE:
<223> OTHER INFORMATION: Synthetic

<400> SEQUENCE: 28

Ser Ala Cys Glu Gln Ile Leu Lys Asp Thr
1               5                   10

<210> SEQ ID NO 29
<211> LENGTH: 22
<212> TYPE: PRT
<213> ORGANISM: Artificial
<220> FEATURE:
<223> OTHER INFORMATION: Synthetic

<400> SEQUENCE: 29

Gly Arg Lys Arg Arg Gln Thr Ser Met Thr Asp Arg Tyr His Ser Lys
1               5                   10                  15

Arg Arg Leu Ile Phe Ser
            20

<210> SEQ ID NO 30
<211> LENGTH: 11
<212> TYPE: PRT
<213> ORGANISM: Artificial
<220> FEATURE:
<223> OTHER INFORMATION: Synthetic

<400> SEQUENCE: 30

Gln Thr Gln Leu Arg Ile Asp Ser Phe Phe Arg
1               5                   10

<210> SEQ ID NO 31
<211> LENGTH: 100
<212> TYPE: PRT
<213> ORGANISM: Artificial
<220> FEATURE:
<223> OTHER INFORMATION: Synthetic

<400> SEQUENCE: 31

Leu Val Phe Glu Ala Pro Asn Gln Glu Lys Val Ser Asp Tyr Glu Met
1               5                   10                  15

Lys Leu Met Asp Leu Asp Val Glu Gln Leu Gly Ile Pro Glu Gln Glu
            20                  25                  30

Tyr Ser Cys Val Val Lys Met Pro Ser Gly Glu Phe Ala Arg Ile Cys
        35                  40                  45

Arg Asp Leu Ser His Ile Gly Asp Ala Val Val Ile Ser Cys Ala Lys
    50                  55                  60

Asp Gly Val Lys Phe Ser Ala Ser Gly Glu Leu Gly Asn Gly Asn Ile
```

```
                65                  70                  75                  80
Lys Leu Ser Gln Thr Ser Asn Val Asp Lys Glu Glu Ala Val Thr
                    85                  90                  95

Ile Glu Met Asn
            100

<210> SEQ ID NO 32
<211> LENGTH: 15
<212> TYPE: PRT
<213> ORGANISM: Artificial
<220> FEATURE:
<223> OTHER INFORMATION: Synthetic

<400> SEQUENCE: 32

Val Ser Asp Tyr Glu Met Lys Leu Met Asp Leu Asp Val Glu Gln
1               5                   10                  15

<210> SEQ ID NO 33
<211> LENGTH: 18
<212> TYPE: PRT
<213> ORGANISM: Artificial
<220> FEATURE:
<223> OTHER INFORMATION: Synthetic

<400> SEQUENCE: 33

Leu Met Asp Leu Asp Val Glu Gln Leu Gly Ile Pro Glu Gln Glu Tyr
1               5                   10                  15

Ser Cys

<210> SEQ ID NO 34
<211> LENGTH: 12
<212> TYPE: PRT
<213> ORGANISM: Artificial
<220> FEATURE:
<223> OTHER INFORMATION: Synthetic

<400> SEQUENCE: 34

Asp Val Glu Gln Leu Gly Ile Pro Glu Gln Glu Tyr
1               5                   10

<210> SEQ ID NO 35
<211> LENGTH: 18
<212> TYPE: PRT
<213> ORGANISM: Artificial
<220> FEATURE:
<223> OTHER INFORMATION: Synthetic

<400> SEQUENCE: 35

Leu Gly Ile Pro Glu Gln Glu Tyr Ser Cys Val Val Lys Met Pro Ser
1               5                   10                  15

Gly Glu

<210> SEQ ID NO 36
<211> LENGTH: 28
<212> TYPE: PRT
<213> ORGANISM: Artificial
<220> FEATURE:
<223> OTHER INFORMATION: Synthetic

<400> SEQUENCE: 36

Leu Gly Ile Pro Glu Gln Glu Tyr Ser Cys Val Val Lys Met Pro Ser
1               5                   10                  15

Gly Glu Phe Ala Arg Ile Cys Arg Asp Leu Ser His
            20                  25
```

```
<210> SEQ ID NO 37
<211> LENGTH: 38
<212> TYPE: PRT
<213> ORGANISM: Artificial
<220> FEATURE:
<223> OTHER INFORMATION: Synthetic

<400> SEQUENCE: 37

Leu Gly Ile Pro Glu Gln Glu Tyr Ser Cys Val Val Lys Met Pro Ser
1               5                   10                  15

Gly Glu Phe Ala Arg Ile Cys Arg Asp Leu Ser His Ile Gly Asp Ala
            20                  25                  30

Val Val Ile Ser Cys Ala
            35

<210> SEQ ID NO 38
<211> LENGTH: 5
<212> TYPE: PRT
<213> ORGANISM: Artificial
<220> FEATURE:
<223> OTHER INFORMATION: Synthetic

<400> SEQUENCE: 38

Arg Tyr Ile Arg Ser
1               5
```